United States Patent [19]
Van Der Puy

[11] Patent Number: 5,986,151
[45] Date of Patent: Nov. 16, 1999

[54] FLUORINATED PROPENES FROM PENTAFLUOROPROPANE

[75] Inventor: Michael Van Der Puy, Amherst, N.Y.

[73] Assignee: AlliedSignal Inc., Morristown, N.J.

[21] Appl. No.: 09/143,133

[22] Filed: Aug. 28, 1998

Related U.S. Application Data

[62] Division of application No. 08/794,984, Feb. 5, 1997.

[51] Int. Cl.$^6$ ............................. C07C 19/08; C07C 17/25
[52] U.S. Cl. ............................................. 570/175; 570/156
[58] Field of Search ..................................... 570/156, 158, 570/175

[56] References Cited

U.S. PATENT DOCUMENTS 3,432,562   3/1969   Gardner .
5,396,000   3/1995   Nappa ..................................... 570/156

FOREIGN PATENT DOCUMENTS 1140928   12/1962   Germany .

OTHER PUBLICATIONS

Henne, A., et al "Influence of a $CF_3$ Group on an Adjacent Double Bond"; J. Am. Chem.Soc. Aug. 1950, vol. 72, p. 3369.
Walker, F., et al. "Dehydrohalogenation of 1,1,1–trihaloethanes", J. Org. Chem., Oct. 1965. vol. 30, p. 3284.
Chemical Abstracts, vol. 71 (1969) 125454y.
Chemical Abstracts, vol. 114 (1991) 114:83236c.
Chemical Abstracts, vol. 114 (1991) 114:125031q.
Chemical Abstracts, vol. 47, (1953) 6858I.
Chemical Abstracts, vol. 97 (1982) 97:144272r.
Chemical Abstracts, vol. 50, (1956) 3194D.
Austin, P., et al, "2–Fluoropropene", J.Am.Chem. Soc.; vol. 75; Oct. 5, 1953; pp. 4834–4835.
Chemical Abstracts, vol. 55, (1961) 349F.
Van Der Puy, M. et al. "Preparation, fluorination and Synthetic Utility of a CFC–olefin Adduct" Journal of Fluorine Chemistry, 76(1996)49–54 Jan., 1996.
Hudlicky, M. "Catalytic Hydrogenolysis of Carbon–Fluorine Bonds: π Bond Participation Mechanism" Journal of Fluorine Chemistry, 44(1989) 345–359.
Lacher, J., et al. "Reaction Heats of Organic Halogen Compounds. VI. The Catalytic Hydrogenation of Some Alkyl Fluorides". J. Phy. Chem. vol. 60, Oct. 1956, pp. 1454–1455.

*Primary Examiner*—Alan Siegel
*Attorney, Agent, or Firm*—Jay P. Friedenson; Marie L. Collazo

[57] ABSTRACT

A process for the preparation of fluorinated propanes and propenes. $CF_3CH=CH_2$ is produced from $CF_3CH_2CHF_2$ by the sequential steps of dehydrofluorination, a reduction, and a second dehydrofluorination in which the same catalyst is preferably used for each step. Preferably the catalysts is palladium on carbon. The process provides the steps of passing $CF_3CH_2CHF_2$ over a Pd/C catalyst to form $CF_3CH=CHF$; hydrogenating $CF_3CH=CHF$ over a Pd/C catalyst to give $CF_3CH_2CH_2F$; and passing $CF_3CH_2CH_2F$ over a Pd/C catalyst to give $CF_3CH=CH_2$.

2 Claims, No Drawings

FLUORINATED PROPENES FROM PENTAFLUOROPROPANE

This application is a division of pending U.S. patent application Ser. No. 08/794,984 filed Feb. 5, 1997.

BACKGROUND OF THE INVENTION

1. Field of the Invention

The present invention pertains to the preparation of fluorinated propanes and tri- and tetra-fluorinated propenes. More particularly, the invention concerns a process for the production of the fluorinated propenes $CF_3CH=CH_2$ and $CF_3CH=CHF$, and the fluorinated propane, tetrafluoropropane $CF_3CH_2CH_2F$.

2. Description of the Prior Art

Fluorinated propenes such as trifluoropropene ($CF_3CH=CH_2$) are useful monomers for the manufacture of fluorosilicones and in the production of fluorinated chemical intermediates such as trifluoropropene epoxide and 3,3,3-trifluoropropylbenzene. Tetrafluoropropene finds use as a copolymer with ethylene, see U.S. Pat. No. 3,472,826 and Chem. Abstr., 71 (1969) 125454y). Tetrafluoropropane (HFC-254fb, $CF_3CH_2CH_2F$) is known as a blowing agent (Chem. Abstr. 114 (1991) P83236c) and heat transfer agent (Chem. Abstr. 114 (1991) P125031q).

Trifluoropropene has been made by two known prior art processes. In both processes the first step is the addition of $CCl_4$ to ethylene to produce $CCl_3CH_2CH_2Cl$. Fluorination of the latter using a liquid phase fluorination process, such as HF in conjunction with an antimony catalyst, provides $CF_3CH_2CH_2Cl$ which is subsequently dehydrochlorinated to give $CF_3CH=CH_2$ (see A. L. Henne, et al, J. Am. Chem. Soc., 72 (1950) 3369). Alternatively, the fluorination of $CCl_3CH_2CH_2Cl$ in a vapor phase process gives $CF_3CH=CH_2$ directly (See German Patent 1 140 928).

Tetrafluoropropene has been made by the dehydroiodination of $CF_3CH_2CHFI$ with alcoholic KOH (R. N. Hazeldine, et al, J. Chem. Soc., (1953) 1199), by the dehydrofluorination of $CF_3CH_2CHF_2$ with KOH (I. L. Knunyants, et al, Izvest, Akad. Nauk S. S. S. R. Otdel. Khim. Nauk., (1960) 1412; Chem. Abstr. 55:349f), and by the addition of HF to trifluoropropyne (R. N. Hazeldine, et al, J. Chem. Soc., (1952) 3483).

Tetrafluoropropane, $CF_3CH_2CH_2F$, has been made by the reaction of ClF with $CCl_3CH_2CH_2Cl$ (N. N. Chuvatkin, et al, Zh. Org. Khim., 18 (1982) 946; Chem. Abstr., 97: 144272r), by the fluorination of $CF_3CH_2CH_2I$ with HgF, and via Zn reduction of $CF_3CH_2CHFI$ (R. N. Hazeldine, et al, J. Chem. Soc., (1953) 1199) or $CF_3CH_2CHFBr$ (P. Tarrant, et al, J. Am. Chem. Soc., 77 (1955) 2783).

The above processes suffer from several drawbacks. These include the use of expensive starting materials or reagents, such as $CF_3I$ or HgF, or hazardous reactants such as ClF. Where dehydrohalogenations are required, a significant amount of waste is produced. For example, in the dehydrofluorination of $CF_3CH_2CHF_2$ with KOH, an organic solvent is generally used, and an excess of KOH is generally employed in order to maintain a concentration of base which results in a high organic conversion. This produces a waste mixture of KOH and KF. While the prior art process for $CF_3CH=CH_2$ appears attractive from the above considerations, it is not readily apparent how it might be used as a suitable raw material for $CF_3CH=CHF$. The use of $CF_3CH=CH_2$ as a raw material for $CF_3CH_2CH_2F$ via HF addition, is not without drawbacks since dimerization may compete with HF addition (see for example, M. Van Der Puy, et al, J. Fluorine Chem., 76 (1996) 49).

Dehydrofluorination of certain hydrofluorocarbons is known. For example, $HCF_2CH_2F$ was dehydrofluorinated over a fluorinated alumina catalyst at about 425° C. and gave mainly $CHF=CHF$ (See U.S. Pat. No. 3,432,562 (1969)). 1,1,1-Trifluoroethane was dehydrofluorinated at 400° C. using NiO, $Fe_2O_3$ or ZnO as the catalyst (See F. H. Walker, et al, J. Org. Chem., 30 (1965) 3284). Conversions were 30 to 63%. Thermal, non-catalytic dehydrofluorinations require substantially higher temperatures. For example, $CH_3CF_2CH_3$ was dehydrofluorinated to $CH_3CF=CH_2$ at 731° C. with a conversion of only 42% (See P. R. Austin, et al, J. Am. Chem. Soc., 75 ((1953) 4834). All of the foregoing disclosures are incorporated herein by reference. It is an object of this invention to overcome the above limitations via a process which is low cost, both from a standpoint of raw material cost and capital cost, which is amenable to scale, and which produces little waste. It is therefore a further objective to provide a process for producing trifluoropropene, tetrafluoropropene and tetrafluoropropane at low cost by utilizing the same or similar process equipment for each reaction step.

SUMMARY OF THE INVENTION

The present invention provides a method for producing 1,1,1,3-tetrafluoropropene which comprises dehydrofluorinating 1,1,1,3,3 pentafluoropropane in the presence of a catalyst and in the absence of a base, under conditions sufficient to produce 1,1,1,3-tetrafluoropropene.

The invention also provides a method for producing 1,1,1,3-tetrafluoropropane which comprises reducing 1,1,1,3-tetrafluoropropene under conditions sufficient to thereby produce 1,1,1,3-tetrafluoropropane.

The invention further provides a method for producing 1,1,1 trifluoropropene which comprises dehydrofluorinating 1,1,1,3-tetrafluoropropane under conditions sufficient to produce 1,1,1-trifluoropropene.

The invention further provides a method for producing 1,1,1-trifluoropropene which comprises reducing 1,1,1,3-tetrafluoropropene under conditions sufficient to thereby produce 1,1,1,3-tetrafluoropropane and then dehydrofluorinating the 1,1,1,3-tetrafluoropropane under conditions sufficient to produce 1,1,1-trifluoropropene.

The invention still further provides a method for producing 1,1,1,3-tetrafluoropropane which comprises dehydrofluorinating 1,1,1,3,3-pentafluoropropane in the presence of a base or a dehydrofluorinating catalyst under conditions sufficient to thereby produce 1,1,1,3-tetrafluoropropene, and then reducing the 1,1,1,3-tetrafluoropropene under conditions sufficient to produce 1,1,1,3-tetrafluoropropane.

The invention also provides a method for producing 1,1,1-trifluoropropene which comprises dehydrofluorinating 1,1,1,3,3-pentafluoropropane in the presence of a base or a dehydrofluorinating catalyst under conditions sufficient to thereby produce 1,1,1,3-tetrafluoropropene, and then reducing the 1,1,1,3-tetrafluoropropene under conditions sufficient to produce 1,1,1,3-tetrafluoropropane, and then dehydrofluorinating 1,1,1,3-tetrafluoropropane under conditions sufficient to produce 1,1,1-trifluoropropene.

DETAILED DESCRIPTION OF THE PREFERRED EMBODIMENT

The first step of the process of this invention requires the dehydrofluorination of $CF_3CH_2CHF_2$ (HFC-245fa) to $CF_3CH=CHF$. As mentioned earlier it is preferable to do this without use of a base such as KOH in order to reduce waste and costs associated with solvent recycle and waste treatment. Ideally, the dehydrofluorination is performed in a manner such that the HF produced can be isolated and recycled. The dehydrofluorination reaction may be conducted in either the liquid or vapor phase, however the vapor phase is preferred. The dehydrofluorination reaction may be conducted by introducing gaseous HFC-245fa into a suitable fluorination reaction vessel or reactor. Since HF is a product of the reaction, the vessel should preferably be constructed from materials which are resistant to the corrosive effects of hydrogen fluoride such as Hastelloy, Inconel, Monel and vessels lined with fluoropolymers. The vessel is packed with a suitable dehydrofluorination catalyst and the vessel heated to reaction temperature.

Catalysts suitable for the dehydrofluorination of $CF_3CH_2CHF_2$ include the base metal oxides such as NiO, $Fe_2O_3$ or ZnO, alumina, chrome oxide, zirconia, titania, activated carbon, and group VIIIA metals supported on carbon or the above metal oxides (such as Pd on carbon or ruthenium on alumina), and mixtures of these catalysts. Metal oxides which react with HF under the conditions of the dehydrofluorination reaction are advantageously pre-treated with HF or an HFC to give a fluorinated or partially fluorinated catalyst, e.g., fluorinated alumina or fluorinated chrome oxide. Dehydrofluorination may occur without this pretreatment, but the product distribution may change until the catalyst has reached a constant composition. Catalytic dehydrofluorinations of hydrofluorocarbons (HFCs) generally require fairly high temperatures. Particularly suitable catalysts for the dehydrofluorination of $CF_3CH_2CHF_2$ include fluorinated alumina, activated carbon, and palladium on carbon. These catalysts provide the desired $CF_3CH=CHF$ in high selectivity at good conversion. While any of the above preferred catalysts are acceptable if only $CF_3CH=CHF$ is desired, if $CF_3CH_2CH_2F$ and/or $CF_3CH=CH_2$ is also desired, then the most preferred catalyst, for reasons of economy and simplicity, is one which can be used for each reaction step. As will be evident from the discussion to follow, the most preferred catalyst is palladium on carbon. Fluorination catalysts having a purity of at least 98% are preferred. The fluorination catalyst is present in an excess but in at least an amount sufficient to drive the reaction. Suitable reaction temperatures range from about 250 to about 600° C., preferably about 350 to about 550° C. and most preferably from about 475 to about 550° C. Reactor pressure is not critical and can be superatmospheric, atmospheric or under vacuum. An inert, diluent gas, such as nitrogen, may be used in mixture with the HFC-245fa, but is not required. The ratio of gaseous reactant to catalyst can be expressed as the linear hourly space velocity (LHSV) or the ratio of the volume of gaseous reactants passed in one hour to the volume of the catalyst bed. In the preferred embodiment, the LHSV ranges from about 1 to about 100 and preferably from about 10 to about 50. A typical LSHV of about 22.4 to about 35.5 corresponds to organic flow rates ranging from about 0.1 to about 0.16 mol/h over a catalyst bed volume of about 100 cc.

In the preferred embodiment, the process flow is in the down direction through a bed of the catalyst. Before each use, the catalyst is preferably dried, pre-treated and activated. It may also be advantageous to periodically regenerate the catalyst after prolonged use while in place in the reactor. Pre-treatment can be done by heating the catalyst to about 250° C. to about 430° C. in a stream of nitrogen or other inert gas. The catalyst may then be activated by treating it with a stream of HF diluted with a large excess of nitrogen gas in order to obtain high catalyst activity. Regeneration of the catalyst may be accomplished by any means known in the art such as, for example, by passing nitrogen over the catalyst at temperatures of from about 100° C. to about b400° C., preferably from about 200° C. to about 375° C., for from about 8 hours to about 3 days depending on the size of the reactor.

The next step in the process of this invention provides for the reduction of $CF_3CH=CHF$ to $CF_3CH_2CH_2F$. The reduction is performed by reacting a stream of gaseous $CF_3CH=CHF$ and hydrogen gas under catalytic conditions at suitable reaction temperatures. In the preferred embodiment, the $CF_3CH=CHF$ and $H_2$ are introduced into a similar reactor as used above which contains a catalyst. The catalyst may be any hydrogenation catalyst. Suitable hydrogenation catalysts non-exclusively include Group VIIIA metals on a support of carbon, or such metal oxides as NiO, $Fe_2O_3$, ZnO, alumina, chrome oxide, zirconia, titania, fluorinated alumina and fluorinated chrome oxide. In the preferred embodiment, the catalyst is the same catalyst used for step one of the overall reaction. The fluorination catalyst is present in an excess but in at least an amount sufficient to drive the reaction. Suitable reaction temperatures range from about −20° C. to about 250° C., preferably from about 20° C. to about 150° C. and most preferably from about 30° C. to about 120° C. Reactor pressure is not critical and can be superatmospheric, atmospheric or under vacuum.

In the preferred embodiment, $CF_3CH=CHF$ is treated with hydrogen using platinum on carbon or platinum on alumina, however the reduction of $CF_3CH=CHF$ using a palladium catalyst is superior since the amount of by-product $CF_3CH_2CH_3$ is much less. In the preferred embodiment, the reduction is conducted at a temperature of from about 25 to about 80° C., more preferably from about 20 to about 150° C. Palladium catalysts are readily available commercially. Palladium can be supported on carbon of various mesh sizes (about 4–8 and about 12–20 mesh sizes are convenient) and palladium loadings generally range from about 0.5 to about 10%. Loadings of about 0.5 to about 2% work well for the reduction of $CF_3CH=CHF$.

The hydrogen to organic ratio required by the reaction stoichiometry is at least about 1, however hydrogen gas is generally supplied in excess. Generally, there is no advantage to employing $H_2$: organic ratios greater than 10:1 and such high $H_2$ flow rates may make it difficult to recover the product. The preferred ratio of $H_2$ to $CF_3CH=CHF$ is from about 1:1 to about 5:1. In the preferred embodiment, the LHSV for the gaseous mixture of $H_2$ and $CF_3CH=CHF$ may range from about 1 to about 100, preferably from about 10 to about 50. In order to reduce operating costs, it is often desirable in a multistep synthesis to use crude product from one step as raw material for the next, thereby eliminating a distillation. For example, the crude product of step 1, comprising unreacted HFC-245fa (bp 15° C.) and $CF_3CH=CHF$ (trans-isomer, bp −16° C., cis-isomer, bp 6° C.) can be used in the reduction step. The HFC-245fa passes through the reactor unchanged, while the $CF_3CH=CHF$ is converted nearly quantitatively to $CF_3CH_2CH_2F$ (bp 29° C.). This eliminates the need to separate $CF_3CH=CHF$ isomers from HFC-245fa by distillation. The mixture of HFC-245fa and $CF_3CH_2CH_2F$ can then be separated by distillation, and the HFC-245fa recycled back to step 1.

The next step of the inventive process is the dehydrofluorination of $CF_3CH_2CH_2F$ to $CF_3CH=CH_2$. This may be performed by reacting $CF_3CH_2CH_2F$ under catalytic conditions at suitable reaction temperatures. In the preferred embodiment, the $CF_3CH_2CH_2F$ is introduced into a similar reactor as used above which contains a catalyst. The catalyst may be any of the above mentioned catalysts which are suitable for dehydrofluorination. In the preferred embodiment, the catalyst is the same catalyst used for steps one and two of the overall reaction. This step may be conducted in a fashion similar to the above described conversion of HFC-245fa to $CF_3CH=CHF$ with some exceptions in the preferred embodiment. In the preferred embodiment, the dehydrofluorination of $CF_3CH_2CH_2F$ is conducted at temperatures which are generally from about 50 to about 100° C. higher than for the dehydrofluorination of $CF_3CH_2CHF_2$. That is, preferred reaction temperatures range from about 300 to about 700° C., preferably about 400 to about 650° C. and most preferably from about 525 to about 650° C. Secondly, and quite unexpectedly, not all catalysts which worked well for the dehydrofluorination of $CF_3CH_2CHF_2$ worked as well for the dehydrofluorination of $CF_3CH_2CH_2F$. In particular, fluorinated alumina and activated carbon catalysts are less preferred. Fluorinated alumina, which resulted in good conversions and selectivities initially, quickly deactivates. Use of activated carbon results in selectivities which are less than obtained with $CF_3CH_2CHF_2$. The most preferred catalyst is palladium on carbon which achieves both good conversion and good selectivity. Palladium on carbon may be used at temperatures in the range of about 450 to about 600° C., and more preferably from about 500 to about 575° C. An inert, diluent gas, such as nitrogen, may be used in mixture with the HFC-245fa, but is not required. When the optional nitrogen is used, it is employed primarily to prevent condensation of $CF_3CH_2CH_2F$ (bp 29° C.) in the feed lines prior to entering the reactor. Nitrogen is also a convenient inert gas to control the total LHSV. In the preferred embodiment, the LHSV ranges from about 1 to about 100, and preferably from about 10 to about 50. Reactor pressure is not critical and can be superatmospheric, atmospheric or under vacuum.

Although not required for the successful conversion of HFC-245fa to $CF_3CH=CH_2$, it is possible and desirable from the standpoint of simplicity and cost to use the same reactor and catalyst for each step of the process. The examples illustrate unexpectedly that, of the catalysts evaluated, palladium on carbon uniquely satisfies the requirements of each reaction step with respect to catalyzing the desired reaction with good conversion and selectivity. Thus it is possible to convert HFC-245fa to $CF_3CH=CH_2$ by first dehydrofluorinating HFC-245fa to $CF_3CH=CHF$, and after separating out the HF and cooling the reactor to a temperature suitable for the reduction, passing crude $CF_3CH=CHF$, along with hydrogen through the reactor to give a mixture of $CF_3CH_2CHF_2$ and $CF_3CH_2CH_2F$. The latter are separated by distillation. The $CF_3CH_2CHF_2$ is recycled to step 1, and the $CF_3CH_2CH_2F$ is fed into the same reactor, reheated to a temperature suitable for the dehydrofluorination to give HF, unreacted $CF_3CH2CH_2F$, and $CF_3CH=CH2$. The latter is finally purified by distillation, while $CF_3CH_2CH_2F$ is recycled to step 3. Since HF is also a commercially valuable material, this process produces little waste. The overall yield for the 3-step process, using non-optimized selectivities given in the following examples, is over 80%. In one embodiment of the invention, the initial dehydrofluorination of HFC-245fa to tetrafluoropropene may be conducted in the presence of a base such as KOH in a method known in the art and then the sequential steps of reducing tetrahydropropene to tetrahydropropane and the dehydrofluorination of the tetrahydropropane to trifluoropropene may be conducted as described above.

The following non-limiting examples serve to illustrate the invention.

I. Conversion of $CF_3CH_2CHF_2$ to $CF_3CH=CHF$

EXAMPLES 1–4

Dehydrofluorination of $CF_3CH_2CHF_2$ Over Activated Carbon

An electrically heated cylindrical Monel reactor of 1" diameter was used in all of the dehydrofluorination examples. Temperature was recorded using a thermocouple placed inside the reactor and within the catalyst bed. Organic was fed into the top of the vertically mounted reactor as vapor and controlled with a calibrated gas flowmeter. Effluent gases were passed through water to absorb HF, a small gas sampling tube and finally a −78° C. cold trap to collect organic products. The progress of the reaction was monitored periodically via GC analysis of the gas sampling tube contents.

Initial scoping experiments indicated that the onset of reaction occurred at about 470° C. (5% conversion at this temperature) and that temperatures in excess of 560° C. were undesirable due to poor selectivity (<75%). In Examples 1–4, intermediate temperature ranges were evaluated using 100 cc of 12–20 mesh activated carbon as the catalyst available as DARCO from Aldrich Chemical Company.

| Example | HFC-245fa flow rate (g/h) | Temp (° C.) | HFC-245fa conversion | Selectivity for c/t-$CF_3CH=CHF$ |
|---|---|---|---|---|
| 1. | 13.5 | 528 | 90% | 83% |
| 2. | 20.4 | 527 | 70% | 94.6% |
| 3. | 13.9 | 512 | 65.6% | 94.5% |
| 4. | 21.2 | 513 | 52.4% | 96.8% |

Examples 1–4 show that activated carbon can be used to dehydrofluorinate HFC-245fa with selectivities for cis- and trans-$CF_3CH=CHF$ of 95% or more at conversions in the range of 50 to 70%. The ratio of trans- to cis-$CF_3CH=CHF$ was typically 3.2:1.

EXAMPLES 5–7

Dehydrofluorination of HFC-245fa Over Fluorinated Alumina

The catalyst used in this example was 100 cc of 1/16–x1/4" fluorinated alumina rods (available from Engelhard Corp.). The catalyst was preconditioned by passing HFC-245fa over this catalyst at 440° C. until HF began to exit the reactor. The temperature was then adjusted as indicated in the table.

| Example | HFC-245fa flow rate (g/h) | Temp (° C.) | HFC-245fa conversion | Selectivity for c/t-$CF_3CH=CHF$ |
|---|---|---|---|---|
| 5. | 13.8 | 340 | 81.6% | 100% |
| 6. | 13.8 | 379 | 93.8% | 99.2% |
| 7. | 13.8 | 400 | 94.9% | 98.9% |

Examples 5–7 indicated that fluorinated alumina, properly conditioned, is an excellent catalyst for the dehydrofluorination of HFC-245fa, permitting lower temperatures to be used compared to activated carbon while maintaining high selectivities at good conversions.

EXAMPLE 8

Dehydrofluorination of HFC-245fa Over a Ruthenium Catalyst

The catalyst used in this example was a mixture of 90 cc activated carbon (as used in Examples 1–4) and 10 cc 15% ruthenium on alumina. The catalyst was preconditioned by passing HFC-245fa at 13.8 g/h over the catalyst at 490° C. until HF exited the reactor. The temperature was then adjusted to 513 C. (conditions nearly identical to those in Example 3). GC analysis indicated a conversion of HFC-245fa of 73% and a selectivity for c/t-$CF_3CH=CHF$ of 99%. Although the results are good, they are only marginally better than the results obtained using activated carbon alone (Example 3).

EXAMPLES 9 AND 10

Dehydrofluorination of HFC-245fa Over a Palladium Catalyst

The catalyst used in Example 9 was 100 cc of 1% Pd on 4–8 mesh carbon. HFC-245fa was passed over this catalyst at a rate of 13.7 g/h at a temperature of 471° C. GC analysis indicated a starting material conversion of 92.4% and a selectivity for c/t-$CF_3CH=CHF$ of 97.2% (the ratio of trans- to cis-$CF_3CH=CHF$ was 4.4:1). In Example 10, the same catalyst was used, but the temperature was 514° C. and the HFC-245fa flow rate was 21 g/h (comparable to Example 4), resulting in a HFC-245fa conversion of 98.8% and a selectivity for c/t-$CF_3CH=CHF$ of 94.3% (trans/cis ratio=4.3:1). Thus Pd on carbon resulted in greater conversion compared with carbon alone, while maintaining high selectivity for the desired c/t-$CF_3CH=CHF$.

II. Reduction of $CF_3CH=CHF$ to $CF_3CH_2CH_2F$

EXAMPLE 11

Reduction over $Pt/Al_2O_3$

The catalyst used in this example was 50 cc of 1% Pt on ⅛" $Al_2O_3$ pellets. The $H_2$ flow rate was 54 cc/min. The $CF_3CH=CHF$ used was pure trans-isomer which was fed into the reactor at 8.9 g/h. At a reaction temperature of 84° C., the initial reactor effluent was >95% $CF_3CH_2CH_3$. This changed with time, producing increasing amounts of $CF_3CH_2CH_2F$. Thus, after 0.7 h the effluent gas (after passing through a water scrubber to remove HF) was comprised of 65% $CF_3CH_2CH_3$, 2.5% $CF_3CH=CHF$, and 28% $CF_3CH_2CH_2F$; after 1.5 h: 51% $CF_3CH_2CH_3$, <1% $CF_3CH=CHF$, 45% $CF_3CH_2CH_2F$; after 3.0 h: 44% $CF_3CH_2CH_3$, <1% $CF_3CH=CHF$, 54% CF3CH2CH2F. The reaction was further evaluated in a temperature range of 37 to 121° C. Similar results were obtained, i.e., conversions were always near 100%, but the selectivity for $CF_3CH_2CH_2F$ was never >60%.

EXAMPLE 12

Reduction Over Pt/C

Pure trans-$CF_3CH=CHF$ was reduced over 50 cc of 0.5% Pt on 4–8 mesh carbon at 110° C. using a hydrogen flow rate of 45 cc/min and organic flow rate of 9.3 g/h. The composition of the exit gas was analyzed at various time intervals with the following results:

| Reaction Time(min) | % Conversion | % $CF_3CH_2CH_3$ | % $CF_3CH_2CH_2F$ |
|---|---|---|---|
| 10 | 97 | 78 | 17 |
| 30 | 100 | 66 | 33 |
| 85 | 99 | 31 | 68 |
| 100 | 100 | 28 | 72 |

Thus the results are somewhat better than those achieved with $Pt/Al_2O_3$ (Example 11), but the selectivity is still unacceptably low.

EXAMPLES 13–17

Reduction of Pure Trans-$CF_3CH=CHF$ Over Pd/C

Pure trans-$CF_3CH=CHF$ was reduced over 50 cc of 1% Pd on 4–8 mesh carbon.

| Ex. No. | $H_2$ rate (cc/min) | Temp (° C.) | $CF_3CH=CHF$ flow rate (g/h) | Conversion (%) | $CF_3CH_2CH_3$ (%) | $CF_3CH_2CH_2F$ (%) |
|---|---|---|---|---|---|---|
| 13 | 73 | 101 | 13.4 | 100 | 1.5 | 98.5 |
| 14 | 80 | 80 | 7.5 | 100 | 0.8 | 99.2 |
| 15 | 59 | 114 | 15.2 | 86.8 | 2.5 | 84.2 |
| 16 | 45 | 50 | 6.6 | 100 | 1.1 | 98.9 |
| 17 | 98 | 70 | 6.6 | 100 | 1.1 | 98.9 |

The results indicate that both conversion and selectivity for CF3CH2CH2F are excellent. Particularly striking is the much lower level of CF3CH2CH3 compared to the same reduction using platinum catalysts.

EXAMPLE 18

Reduction of a Mixture of c/t-$CF_3CH=CHF$ AND HFC-245fa

Using the same catalyst used in Examples 13–17, a mixture of 44.5% HFC-245fa, 43.9% trans-$CF_3CH=CHF$, and 11.2% cis-$CF_3CH=CHF$ was hydrogenated at 35–38° C. The $H_2$ flow rate was 44.3 cc/min, while the organic mixture was fed into the reactor at 9.2 g/h. The conversion of $CF_3CH=CHF$ isomers was 100% and the selectivity for $CF_3CH_2CH_2F$ approximately 98%. The crude product, collected in a −78° C. trap was comprised of a mixture of HFC-245fa and $CF_3CH_2CH_2F$. Distillation gave $CF_3CH_2CH_2F$, bp 29 C., in >98% purity.

III. Dehydrofluorination of $CF_3CH_2CH_2F$

EXAMPLE 19 AND 20

Dehydrofluorination Over Activated Carbon

The reactor and catalyst used in the dehydrofluorination of CF3CH2CH2F are the same as described in Example 1. The conditions used and the results obtained are tabulated below.

| Example | Temp (° C.) | $N_2$ (cc/min) | Organic (%) | Conversion (g/h) | Selectivity (%) |
|---|---|---|---|---|---|
| 19 | 500 | 53 | 20 | 9.4 | 74.5 |
| 20 | 548 | 44 | 20 | 31.6 | 78.5 |

The results indicate that, compared to $CF_3CH_2CHF_2$, the dehydrofluorination of $CF_3CH_2CH_2F$ requires a higher temperature to achieve similar conversions.

EXAMPLE 21

Dehydrofluorination of $CF_3CH_2CH_2F$ Over Fluorinated Alumina

The reactor and catalyst were the same as in Examples 5–7. At 450° C., using an organic flow of 18.9 g/h and a nitrogen flow of 63 cc/min, the initial conversion was high, but the catalyst deactivated rapidly:

| Time | Conversion | Selectivity for $CF_3CH=CH_2$ |
| --- | --- | --- |
| 19 min | 100% | 89% |
| 40 min | 92% | 96% |
| 60 min | 74% | 97% |
| 73 min | 61% | 97% |

Similarly, at 484° C.:

| | | |
| --- | --- | --- |
| 10 min | 50% | 95.6% |
| 20 min | 26% | 96.9% |
| 60 min | 17% | 96% |

Thus, although the selectivity was high, fluorinated alumina in an unattractive catalyst for the dehydrofluorination of $CF_3CH_2CH_2F$, even though it appears to be an excellent catalyst for the dehydrofluorination of $CF_3CH_2CHF_2$ where rapid catalyst deactivation was not observed.

EXAMPLES 22 AND 23

Dehydrofluorination Over Palladium on Carbon

Example 23. The catalyst used in this example was 100 cc of 1% Pd on 4–8 carbon (used in Examples 9 and 10). At 528 C., with a $CF_3CH_2CH_2F$ flow rate of 22.3 g/h and a nitrogen flow rate of 44 cc/min, the conversion was 50%, while the selectivity for $CF_3CH=CH_2$ was 83%. Thus, both conversion and selectivity were superior to activated carbon alone (compare Examples 19 and 20).

EXAMPLE 24

In a manner similar to that above, a conversion of 75% and a selectivity for $CF_3CH=CH_2$ of 84% was obtained at a reaction temperature of 537° C., an organic feed rate of 23.8 g/h, and a nitrogen flow rate of 71 cc/min.

EXAMPLE 25

To a slurry of 9.4 g $AlCl_3$ in 90 mL benzene cooled in an ice bath, was added (over 18 minutes) a solution of 14.2 g of $CF_3CH_2CH_2F$ in 10 mL benzene. The mixture was stirred for an additional 0.5 hour at ice-bath temperature and 1 hour at room temperature. It was then poured into 50 g ice and 25 mL concentrated HCl, and the resulting solution stirred until the color disappeared. The benzene layer was separated, washed with 25 mL saturated NaCl and dried ($Na_2SO_4$). Distillation provided 1,1,1-trifluoro-3-phenylpropane ($CH_3CH_2CH_2Ph$), bp 77–79° C. at 32 mm Hg. $^1H$ NMR: 7.1(5H), 2.8(m) ppm. $^{19}F$ NMR: −67.2 (t, J=9.7 Hz) ppm. This example shows the utility of $CF_3CH_2CH_2F$. It illustrates that it can be used in a Friedel-Crafts reaction to make the same product as would be obtained if $CF_3CH=CH_2$ had been used.

What is claimed is:

1. A method for producing 1,1,1-trifluoropropene which comprises dehydrofluorinating 1,1,1,3,3-pentafluoropropane in the presence of a catalyst comprising palladium on carbon under conditions sufficient to thereby produce 1,1,1,3-tetrafluoropropene, and then reducing the 1,1,1,3-tetrafluoropropene under conditions sufficient to produce 1,1,1,3-tetrafluoropropane, and then dehydrofluorinating 1,1,1,3-tetrafluoropropane under conditions sufficient to produce 1,1,1,-trifluoropropene.

2. The method of claim 1 wherein each reaction is conducted in the presence of a catalyst which comprises palladium on carbon.

* * * * *